United States Patent [19]

O'Neill

[11] 4,154,247
[45] May 15, 1979

[54] FORMABLE CARDIAC PACER LEAD AND METHOD OF ASSEMBLY AND ATTACHMENT TO A BODY ORGAN

[75] Inventor: Edward G. O'Neill, St. Paul, Minn.
[73] Assignee: Medtronic, Inc., Minneapolis, Minn.
[21] Appl. No.: 783,689
[22] Filed: Apr. 1, 1977
[51] Int. Cl.² .............................................. A61N 1/04
[52] U.S. Cl. ................................................. 128/419 P
[58] Field of Search ..................... 128/418, 419 P, 404

[56] References Cited
U.S. PATENT DOCUMENTS

| | | | |
|---|---|---|---|
| 3,348,548 | 10/1967 | Chardack | 128/418 |
| 3,890,977 | 6/1975 | Wilson | 128/419 P |

Primary Examiner—William E. Kamm
Attorney, Agent, or Firm—Cameron, Kerkam, Sutton, Stowell & Stowell

[57] ABSTRACT

A cardiac pacer lead is disclosed as being formable at the time of pacer implantation by the attending surgeon, by heating the pacer lead, as in boiling water, and then forming or shaping it to the desired configuration so that a pacer electrode is maintained resiliently in contact with the inner surface of the patient's heart, e.g. his atrium. The pacer lead comprises at least one flexible conductor about which is disposed a first insulating layer of a repeatably thermally-activated material to permit its formation into a desired configuration, and a second insulating layer disposed thereabout of a character suitable for implantation within the patient's body, i.e., resistant to corrosion by body fluids. Further, there is disclosed the method of assembling and attaching the cardiac pacer lead to a body organ, e.g., the patient's heart. The method includes the steps of incorporating the thermally-activated material within the pacer lead, heating the lead and shaping the lead into a non-linear configuration, reforming the lead into a linear configuration, inserting the lead to make electrical contact with the body organ and discontinuing the straightening of the pacer lead.

16 Claims, 11 Drawing Figures

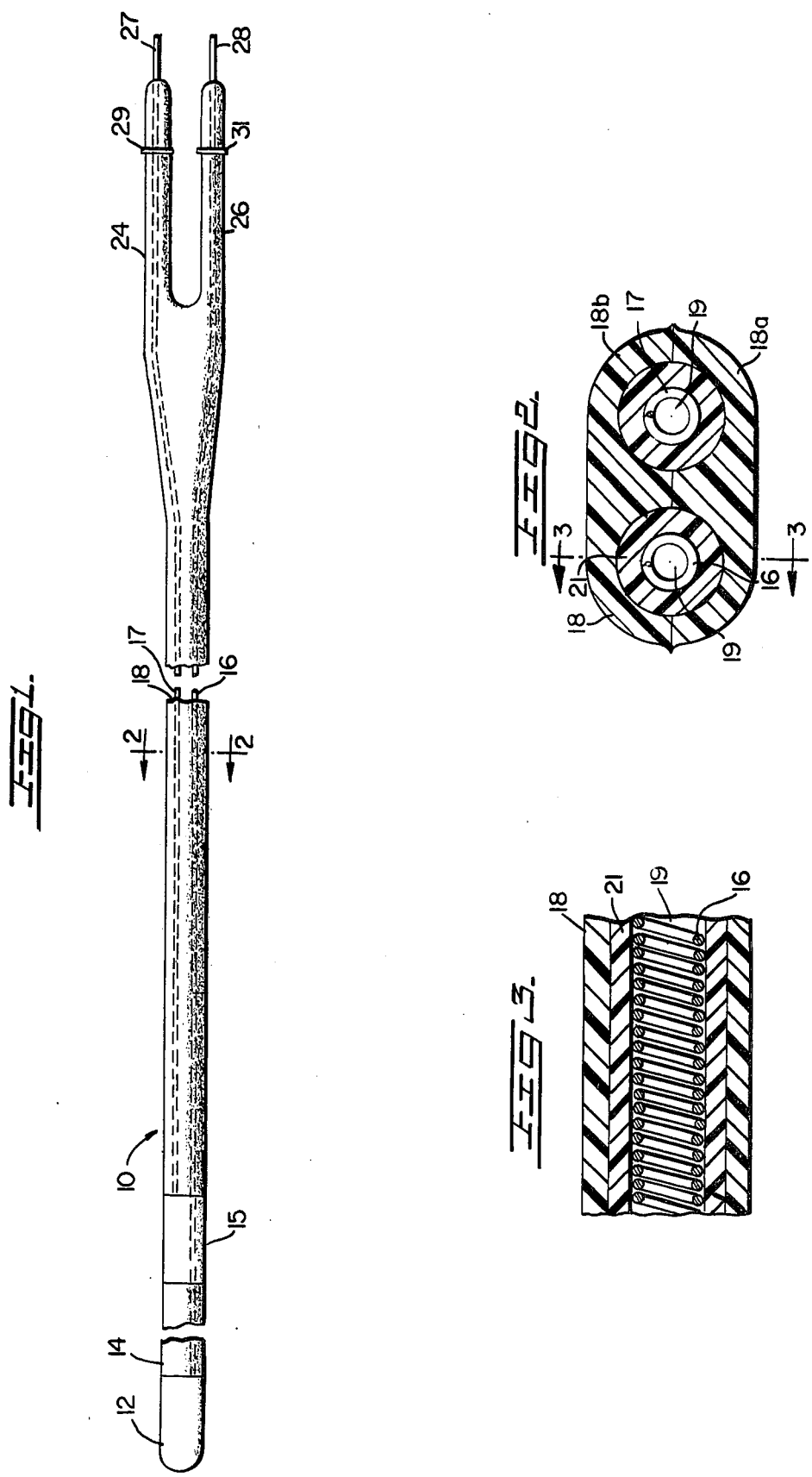

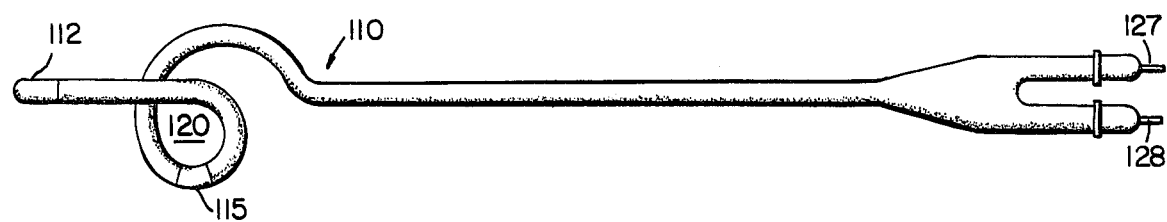
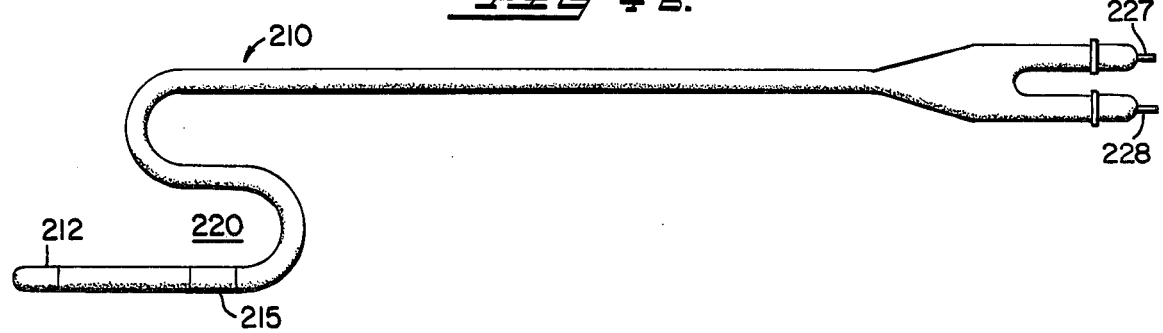
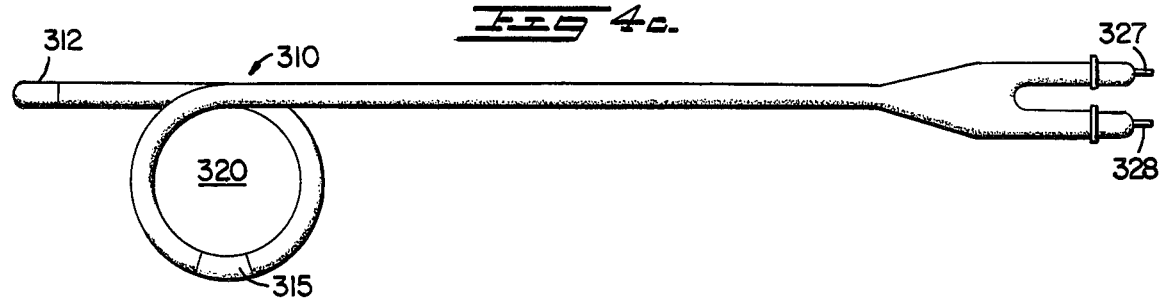
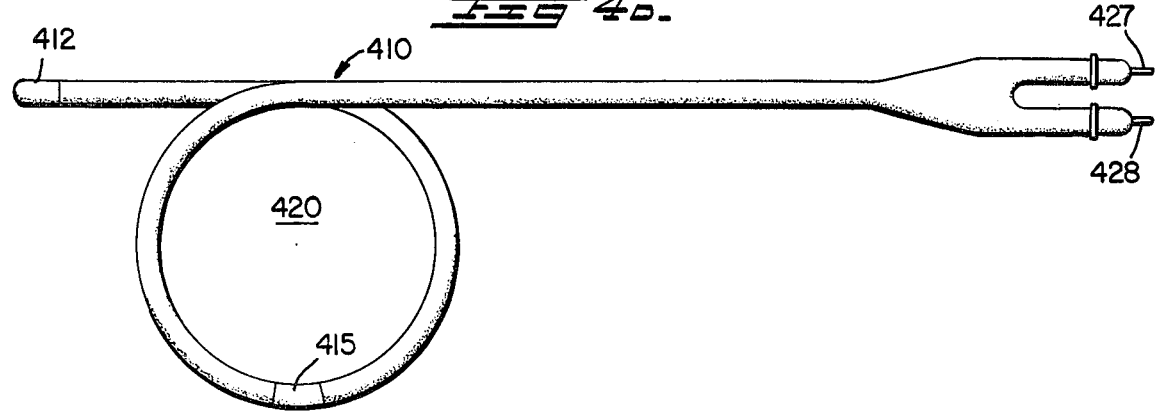

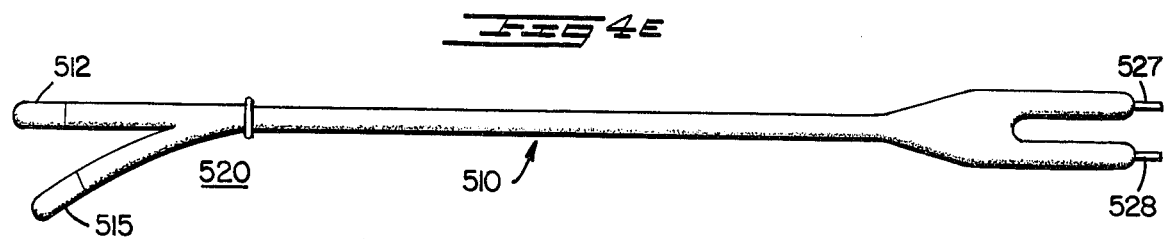
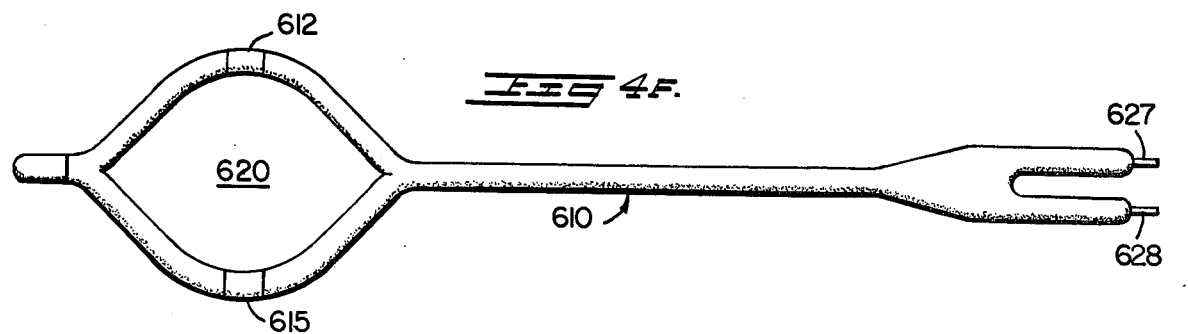
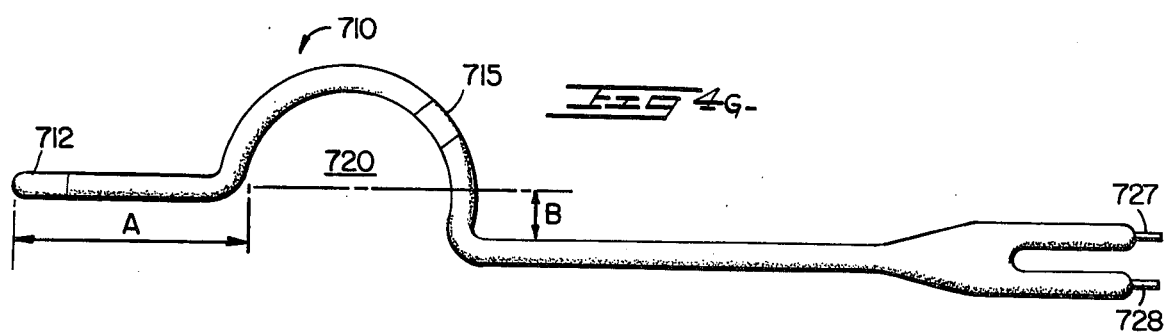
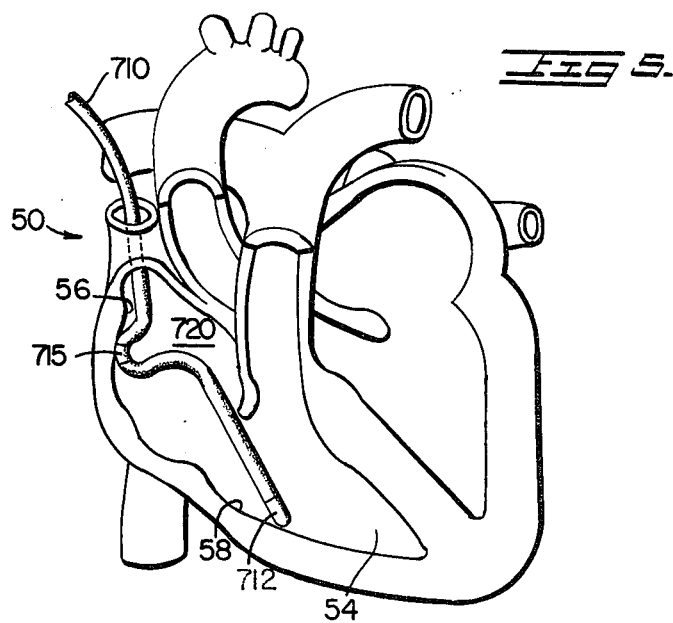

FORMABLE CARDIAC PACER LEAD AND METHOD OF ASSEMBLY AND ATTACHMENT TO A BODY ORGAN

BACKGROUND OF THE INVENTION

1. Field of the Invention

This invention relates to the field of medical electronics and particularly to cardiac pacer leads adapted to be formed in a variety of configurations by a relatively simple method, at the time of implantation.

2. State of the Art

Electrical stimulation of body tissue and organs is a method of treating various pathological conditions which is becoming quite commonplace. Such stimulation generally calls for making some type of electrical contact with the body tissue or organ. In particular, with respect to the heart, electrical pacer leads are physically coupled or implanted into the myocardial or endocardial tissues.

In order to attach the output electrodes of a heart pulse generator or pacer to the heart, it is necessary to make an incision in the neck whereby the leads of an external or an implanted pacer may pass through the patient's subclavian vein and into the patient's heart. The leads used for such purpose typically have long, thin, flexible conductors, typically of a helical configuration, enclosed by an insulating material of a character suitable for implantation within the patient's body. At the distal end of such leads, the flexible conductor is connected to an electrode capable of being placed in contact with the patient's heart. In some lead configurations, typically known as "bipolar leads", two such flexible conductors are included within one insulating covering, thereby providing a forward conduction path and a return path for electrical stimulation to the heart. For this type of lead, distal and proximal electrodes are provided, spaced from each other in order to make contact with separate portions of the heart, e.g. the atrium and ventricle of the patient's heart. To this end, the lead is inserted through the patient's subclavian vein and into his heart, with the distal electrode coming to rest in the ventricle cavity. The distal electrode so inserted normally will be confined to the ventricle without difficulty. However, as noted by U.S. Pat. No. 3,729,008, the proximal electrode for stimulating the atrium has difficulty in maintaining its position within the confines of the atrial cavity. In this regard, the atrium has smooth walls, allowing easy slippage of an ordinary linear electrode. U.S. Pat. No. 3,729,008 suggests placing a curve in the pacer lead of a shape and dimension to conform the lead to the atrium and to be suitable for gripping the moving atrium wall, whereby good electrical contact is maintained between the proximal electrode and the undulating, flexible atrium wall of the patient's heart. Further, the noted patent suggests that the pacer lead be made of a medical-grade, resilient rubber that is formed by a process such as vulcanization or injection molding. It is recognized that such medical-grade, silicon rubber is selected in order to provide a material resistant to corrosion by the body fluids to the patient in which such lead is implanted.

In U.S. Pat. No. 3,596,662 of Bolduc, assigned to the assignee of this invention, there is disclosed a method of molding a pacer lead having electrical conductors encapsulated in a unitary, homogeneous body of flexible, non-conductive plastic material, such as silicone rubber. This process of forming the pacer lead utilizes a 3-piece mold comprising a pair of identical female molds and a male mold, the female molds having elongated cavities of a size and shape of one-half of the pastic body covering the conductors. The male mold has elongated ribs, each of which has a volume equal to one-half of the volume occupied by the conductors, plus one-half of any volume to be left void. Halves of the pacer leads are initially made by mounting the male mold in an assembled relation with the female mold and injecting the silicone rubber into the mold cavity under high pressure. The male mold then is removed from the female mold, exposing the grooves in the molded halves of the silicone rubber bodies. Thereafter, the conductors are placed between the halves of the bodies in alignment with the grooves formed by the ribs of the male mold. The conductors are encapsulated in the body by combining the halves of the body into a one-piece member by simultaneously subjecting the assembled female molds to a high pressure and temperature sufficient to cause the mating halves of silicone rubber to adhere to each other.

The use of such a method of forming pacer leads has proved very advantageous, especially with the use of linear or straight pacer leads. However, it is desirable to form such pacer leads with a variety of configurations in order to permit the retention of the lead's electrode within the patient's heart and in particular, to permit the resilient placement of the atrial or proximal electrode against the inner flexing wall of the patient's atrium. It has been contemplated to adapt the method as taught in U.S. Pat. No. 3,596,662 to the formation of such curved pacer leads. However, the formation of the 3-piece molds in such a non-linear configuration would be unduly expensive in that the machining of such molds into the desired curves would be expensive and time-consuming. Further, it is contemplated that in the course of the surgical procedure by which the heart pacer and pacer lead are inserted within the patient, the attending surgeon may find it desirable to form the pacer lead into one configuration or another or to vary the size of a particular configuration in order to adapt the pacer lead to a particular patient. If a pacer lead made of a conventional silicone rubber coating is used, such forming of the pacer lead at the time of implantation would be impractical in that once cured, the silicone rubber is set in its normal, linear configuration and would not maintain the desired configuration.

SUMMARY OF THE INVENTION

It is therefore an object of this invention to provide a pacer lead that is capable of being formed into a variety of configurations by the attending surgeon.

It is a more specific object of this invention to provide a pacer lead that is capable of being manufactured by relatively low-cost molding techniques and at a subsequent time, i.e., at the time of implantation within a patient, of being formed into a variety of configurations by the attending surgeon by relatively simple techniques. It is a further object of this invention to provide a new and novel method of assembling a pacer lead and of inserting it within the patient to make contact with a body organ, e.g., the patient's heart.

In accordance with these and other objects of the invention, there is provided a pacer lead comprising a flexible conductor extending between a first contact adapted to be connected to a cardiac pacer and an electrode adapted to be coupled to the patient's heart, and covered by a first insulating layer made of a repeatably heat-deformable material, e.g. a polypropylene, polyethylene, polyurethane or other thermally-deformable materials, and a second insulating layer disposed thereabout of a high medical-grade material, such as silicone rubber, that is adapted to be inserted within the patient's body. In one aspect of this invention, the method of assembly and insertion includes the steps of including the first insulating layer within the pacer lead, thereafter, the attending physician forms the pacer lead into a variety of configurations particularly adapted to the patient, by first heating the pacer lead, e.g. disposing the lead in boiling water, thereafter forming it into a selected configuration of size and shape particularly adapted to his patient, and permitting the lead to cool to room temperature, thus setting the pacer lead to the selected configuration. Thereafter, the physician straightens the lead for insertion within the patient's body and attachment to a body organ. Thereafter, the straightening is discontinued, whereby the pacer lead returns to its selected configuration to make efficient electrical contact with the patient's body organ.

In one particular embodiment of this invention, a bipolar lead is suggested whereby first and second conductors of a flexible, helical configuration extend from respective first and second pacer contacts to a distal or ventricular electrode and to a proximal or atrial electrode, respectively. Each of the first and second conductors has a heat-deformable insulating layer disposed thereabout. At the time of implantation, the attending surgeon configures the leading end of the cardiac pacer lead into a variety of configurations wherein the proximal or atrial electrode is offset in a curved configuration, whereby it is disposed against the inner surface of the beating atrium to maintain efficient electrical contact therewith.

BRIEF DESCRIPTION OF THE DRAWINGS

These and other objects and advantages of the present invention will become more apparent by referring to the following detailed description and accompanying drawings, in which:

FIG. 1 is a plan view of a pacer lead in accordance with the teachings of this invention;

FIG. 2 is an enlarged sectional view taken along the line 2—2 of FIG. 1;

FIG. 3 is a sectional view taken along the line 3—3 of FIG. 2;

FIGS. 4A-4G show various configurations into which the leading portion of the cardiac pacer lead of this invention may be formed; and FIG. 5 shows the manner in which the pacer lead of FIG. 4G may be inserted within the patient's heart in order that its proximal or atrial electrode may be disposed effectively into contact with the patient's heart.

DETAILED DESCRIPTION OF THE PREFERRED EMBODIMENTS

With regard to the drawings and in particular to FIG. 1, there is shown an elongated pacer lead indicated generally by the numeral 10, suitable for connecting a cardiac pacer to the patient's heart. Leads used in this environment must withstand constant, rapid flexing over long periods of time and repeated lateral and axial flexing without fatiguing and elongation caused by body motion as well as the motion of the heart. Lead 10 comprises a pair of first and second electrical conductors 16 and 17. An insulating layer 21, as shown in FIGS. 2 and 3, is disposed about each of the electrical conductors 16 and 17 and has the property of being repetitively heat-deformable to permit shaping of the leading end portion of the lead 10, in a manner as will be more fully explained. Further, a second insulating covering 18 is disposed about or encapsulates the electrical conductors 16 and 17 to form a unitary lead 10, as more fully illustrated in FIG. 2. The leading end of the pacer lead 10 includes at its tip a first or distal electrode 12, particularly adapted in one illustrative embodiment of this invention for making effective electrical contact with the ventricular section of the patient's heart. At a point spaced from the distal electrode 12, there is disposed a second or proximal electrode 15, which in one embodiment of this invention is particular adapted, as by forming the lead 10 into any of a variety of configurations, for efficient electrical contact with the atrial section of the patient's heart. The distal and proximal electrodes 12 and 15 are separated from each other by a layer 14 of insulating material, and are electrically connected, respectively, to the flexible conductors 17 and 16. At the opposite end of the pacer lead 10, it is split or bifurcated into a pair of legs 24 and 26. Projected longitudinally from the ends of the legs 24 and 26 are cylindrical contacts 27 and 28 used to connect the lead 10 to the contacts of the cardiac pacer or pacemaker. The legs 24 and 26 adjacent the contacts 27 and 28, have collars 29 and 31 which function as stops and seals for the connection to the pacer.

Referring now to FIGS. 2 and 3, there are shown cross-sections of the lead 10 particularly illustrating the significant aspects of this invention. In particular, each of the flexible electrical conductors 16 and 17 is formed as a helical coil having an open passageway or lumen 19 disposed axially therealong to permit a stylet or stiff wire to be threaded into the lead to provide the lead 10 with stiffness and maneuverability, enabling its insertion in an operating procedure, as will be explained in detail later. Each conductor 16 and 17 is enclosed with the first insulating layer 21 made of a material having a repeatable, heat-deformable quality so that upon heating, it may be repeatedly deformed, whereby the lead 10 may be disposed in a variety of configurations. In an illustrative embodiment of this invention, the insulating material of layer 21 may be a polypropylene, polyethylene and/or polyurethane. Further, the insulating, coated conductors 16 and 17 are encapsulated in a body 18 of an insulating material that is suitable for implantation within a patient, i.e., resistant to corrosion by body fluids. This material comprising the body is a vulcanizable, flexible material and in one illustrative embodiment of this invention, may be a silicone rubber, such as Silastic 0372, attainable from Dow-Corning. The insulating material of layer 21 is compatible with the insulating material of the body 18, in the sense that the insulating material of layer 21 is deformable at a temperature that will not adversely affect the insulating material of body 21, i.e., to cause it to burn, tear, decompose or otherwise deteriorate. In the illustrative embodiment wherein the body 18 is made of the noted silicone rubber, it is recognized that such a material should not be heated to a temperature greater than approximately 600° F., this temperature being a maximum safe limit to protect the integrity of the silicone rubber. Noting that it is desirable generally to maintain the temperature of the silicone rubber to be less than its maximum safe limit, the insulating material of the layer 21 should be heated to a temperature not greater than 400° F., when utilized with a body 18 of silicone rubber. In one illustrative embodiment of this invention wherein the lead 10 is to be implanted within a patient's heart, the repeatedly deformable insulating material of layer 21 should be selected so that it is not adversely affected at temperatures in the order of that of the human body, i.e., 98.6° F. Noting that repeatedly deformable materials may exhibit the characteristic known as "creep", wherein the material slowly loses its shape, it is desired that the insulating material of layer 21 be heat-deformable at temperatures in excess of 200° F. so that it may exhibit a high creep resistance at temperatures in the order of that of the human body. In another illustrative embodiment of this invention, the spring conductors may be made of a suitable, electrically-conductive material having a low electrical resistance, such as a platinum-iridium alloy. This alloy may comprise 90% platinum and 10% iridium.

Illustratively, the method of manufacture may be similar to that disclosed in U.S. Pat. No. 3,596,662, entitled "Electrode for Cardiac Stimulator", by Lee R. Bolduc and assigned to the assignee of this invention, wherein a 3-piece mold is utilized comprising a pair of identical female molds and a male or core mold. Initially, the first female mold is filled with the aforedescribed silicone rubber and the male mold is disposed on top thereof to form a pair of grooves along the length of a bottom half 18a of the body 18 for receiving the conductors 16 and 17, as covered with the first insulating layers 21. After completion of the bottom half 18a of the body 18, each of the conductors 16 and 17 is inserted within the cylindrically or tube-shaped insulating layers 21, and thereafter is disposed within the grooves of the bottom half 18a of the body 18. Thereafter, the second half 18b of the insulating body 18 is disposed upon the first half 18a, and the composite is subjected to heat of a temperature of 300° F. for approximately 3 minutes, until the two halves 18a and 18b fuse or vulcanize together about the conductors 16 and 17 as covered by the layers 21 of insulating material. For a detailed explanation of a suitable method by which the lead 10 of this invention may be manufactured, reference is made to the aforementioned U.S. Pat. No. 3,596,662, which is specifically incorporated herein by reference.

The material of which the body 18 is made, as described above, is particularly adapted to be inserted within the human body and protects the conductors 16 and 17 from the body fluids. After being fused at the aforedescribed temperature, the silicone rubber is set or cured, and upon additional heating, will not change its configuration. However, the layers 21 of a repeatably heat-actuatable material may be repeatedly heated, as by being disposed in boiling water, and thereafter, reformed into a new configuration; upon cooling to room temperature or to body temperature, the layer 21 will maintain its new configuration, thus imparting its configuration to the lead 10.

In a typical surgical procedure for the implantation of the lead 10, an opening is made in the patient, to expose his jugular vein. Originally, the lead 10 is supplied to the attending surgeon as an essentially linear element, as shown in FIG. 1. However, it is desired to impart a configuration or irregularity to the shape, whereby the second or proximal electrode 15 may be held in efficient electrical contact with the interior wall of the heart and in particular, the patient's atrium. The attending surgeon reheats the lead 10 and in particular the layers 21 of a repeatably, thermally-actuated material, whereby the material of layers 21 becomes deformable and the surgeon may form the entire lead 10 into a desired configuration, as variously illustrated in FIGS. 4A-4G. In each, it is noted that the proximal electrode, i.e., the electrode that is indicated by the numeral whose last two digits are 15, is displaced from the line along which the lead extends. In an illustrative embodiment of this invention wherein the body 18 is made of polyurethane, the lead is heated in an oven to 300° F., without adversely affecting the layer 21 of silicone rubber. The heating of the lead may also be accomplished by placing the lead into a container of boiling water. While the lead is still heated, the physician configures the lead into the desired configuration, dependent upon the patient in terms of his physical size and his heart's condition. After cooling, the lead 10 maintains the shaped configuration. At this point, a stylet is inserted within at least one of the lumens or passageways 19, whereby the lead is made of a substantially linear configuration to permit its insertion through the jugular vein and into a patient's heart 50, as illustrated in FIG. 5. In particular, the electrode 710, as more fully illustrated in FIG. 4G, is inserted so that its distal or ventricular electrode 712 is inserted within the heart 50 and into the ventricle 54, whereby the electrode 712 makes efficient electrical contact with the inner surface 58 of the ventricle 54. After insertion within the patient's heart, the stylet is withdrawn from the lumen of the lead 710, permitting it to assume its configuration or discontinuity 720 wherein the lead 710 displaces the proximal or atrial electrode 715, so that it is disposed against an inner wall 56 of the atrium in a manner to permit efficient electrical contact between the inner wall 56 and the atrial electrode 716. It is noted that the desired curve and dimension between the ventricular and atrial electrodes 712 and 715 are carefully selected to permit efficient electrical contact to the wall 56, which is rather smooth and is continually flexing as the heart 50 beats. In accordance with the teachings of this invention, the configuring of the lead 710 is permitted at the time of the surgical implantation by the attending surgeon, who may adjust the configuration to suit the condition of the particular patient's heart.

Further, in contrast to the prior art, the lead of this invention is initially formed in a linear fashion, as is the electrode 10 of FIG. 1, and is thereafter formed. Thus, the molds, as described above and also in the above-identified U.S. Pat. No. 3,596,662, of an essentially linear configuration may be used, and it is not necessary to use molds that are formed in the desired configuration whose construction is, of necessity, of greater expense and complexity. Further, the use of the lead of this invention allows the attending physician to conform the lead at the time of implantation to the particular needs of the patient in which the lead is being inserted.

Illustratively, the surgeon may configure the lead into a variety of configurations as shown in FIGS. 4A-4G, whose numerals correspond to those of FIGS. 1-3, but whose hundredth's digit has been changed to indicate a new embodiment. In FIG. 4A, the lead 110 has an essentially circular configuration 120, with the center of the configuration 120 being disposed essentially along the length of the lead 110, and the proximal or atrial electrode 115 being displaced approximately a radial distance from its center. In FIG. 4B, a lead 210 is disposed in an essentially S-shaped configuration, with the atrial electrode 215 displaced essentially the height of the S from the length of the lead 210. The leads 310 and 410 of FIGS. 4C and 4D are of circular configurations 320 and 420, with the center of the circular configurations 320 and 420 being displaced from the length of the leads 310 and 410; the essential difference between the leads 310 and 410 being in the size of the circular configurations 320 and 420. In each case, the atrial electrodes 315 and 415 are displaced essentially a length corresponding to the diameter of the circular configurations 320 and 420 from the extent of the leads 310 and 410, respectively. In FIG. 4E, the configuration 520 of the lead 510 bifurcates the leading end of the lead 510 with a leg along which the conductor bearing the atrial or proximal electrodes 515 being curved. In FIG. 4F, a split configuration 620 is shown wherein the leading portion of the lead 610 is united at its end with a slit separating the electrical conductors leading to the first and second electrodes 612 and 615, which both are adapted to contact a single portion, i.e., either the atrial or ventricular portion of the patient's heart. In this embodiment, stylets are inserted through the lumens associated with both of the conductors of the electrode 610 to straighten the configuration 620 to permit its insertion in either the atrium or ventricle of the patient's heart, and thereafter is removed, whereby the straightened configuration 620 springs back to the configuration as shown in FIG. 4F. In FIG. 4G, there is shown the lead 710 having an "earthworm" configuration 720, wherein an essentially U-shaped curve 720 is disposed within the lead 710. In particular, the configuration 720 is not completely symmetrical with the trailing portion of the configuration 720 closest to the contacts 727 and 728, being offset by a dimension "B" from the leading portion of the lead 710 associated with the ventricular electrode 712. In an illustrative configuration of this invention, wherein the lead 710 is adapted to be inserted into a heart as shown in FIG. 5 with the electrode 712 in contact with the ventricle and the electrode 715 in efficient contact with the patient's atrium, the length according to the dimension "A" of the leading portion of the electrode 710 is selected to be 8.89cm, whereas its displacement from the length of the lead 710, according to dimension "B" as shown in FIG. 4G, is selected to be 6.35cm, such dimensions assuring the desired interconnection to the atrial and ventricular portions of the patient's heart as shown in FIG. 5.

Thus, there has been shown a pacer lead capable of being readily inserted within a patient's body in a manner to permit efficient electrical contact with the interior walls of the patient's heart. In one illustrative bipolar embodiment of this invention, the lead includes a distal or ventricular electrode, and a proximal or atrial electrode, and the lead is configured to displace the atrial portion of the lead so that the atrial electrode may be disposed in intimate contact with the interior wall of the patient's atrium, while permitting the leading portion of the lead containing the ventricular electrode to be inserted into the patient's ventricle. It is further understood that the lead also may be formed as a coaxial or unipolar lead for other medical applications.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A body implantable lead adapted to transmit electrical signals, said lead having an initial, substantially linear configuration, said lead comprising:
    (a) an electrically conductive electrode for being disposed in electrical contact with a body organ;
    (b) a flexible electrical conductor having a predetermined length and electrically coupled to said electrode;
    (c) first means coupled to said lead and actuatable in response to the application of heat and force for being shaped initially to impart to said lead a first, non-linear configuration to dispose said electrode in efficient contact with a desired portion of the body organ, said first means comprising a flexible, insulating material; and
    (d) second means for providing an electrically insulating, protective surface inert to body fluids and tissues and disposed about said lead, said insulating material having the property of being shaped at a temperature less than that temperature at which said second means is adversely affected.

2. A body implantable lead as claimed in claim 1, wherein said first means comprises an insulating layer disposed about said electrical conductor and made of a repeatably heat-deformable insulating material.

3. A body implantable lead as claimed in claim 1, wherein said insulating material of said first means has the property of being heat-deformable at a temperature greater than body temperature.

4. A body implantable lead as claimed in claim 2, wherein said insulating material comprises polyethylene.

5. A body implantable lead as claimed in claim 2, wherein said insulating material comprises polyurethane.

6. A body implantable lead as claimed in claim 2, wherein said insulating material comprises polypropylene.

7. A cardiac pacer lead adapted for applying electrical stimulation from a cardiac pacer to the ventricular and atrial portions of a patient's heart, said pacer lead having a first, substantially linear configuration, said lead comprising:
    (a) first and second electrically conductive contacts for being coupled to the ventricle and atrium stimulating portions of the patient's cardiac pacer;
    (b) first and second electrically conductive electrodes for being disposed, respectively, in efficient electrical contact with the ventricular and atrial portions of the patient's heart;
    (c) first and second electrical conductors each having leading and trailing end portions and affixed to and electrically coupled, respectively, to said first contact and electrode, and said second contact and electrode;
    (d) first means comprising a covering disposed about said first and second electrical connectors and made of a first flexible, shapeable insulating material and actuable in response to the application of heat of a given temperature for being disposed to a second configuration to impart to said pacer lead a selected, corresponding configuration whereby a portion of said pacer lead corresponding to said leading portion of said conductors is offset with respect to the remaining portion thereof so that said second electrode may be offset with respect to the trailing portion thereof, maintaining said second electrode in efficient electrical contact with the atrial portion of the patient's heart; and (e) second means for providing a protective surface about said pacer lead and made of a second insulating material resistant to corrosion by the patient's body fluids, said temperature being less than that temperature at which said second insulating material is degraded.

8. The cardiac pacer lead as claimed in claim 7, wherein said first means comprises a covering disposed about said first and second electrical connectors and made of a flexible, shapeable insulating material.

9. The cardiac pacer lead as claimed in claim 8, wherein said insulating material of said second means comprises a silicone rubber.

10. The cardiac pacer lead as claimed in claim 7, wherein said leading portion of said pacer lead is configured in a substantially circular configuration, whereby said second electrode is displaced from said trailing portion of said pacer lead.

11. The cardiac pacer lead as claimed in claim 7, wherein said pacer lead is configured in a substantially S-shaped configuration, whereby said second electrode is displaced from the direction of extent of said trailing portion of said pacer lead.

12. The combination of a body implantable lead adapted to transmit electrical signals, said lead having a first substantially linear configuration, and rigid means for maintaining said body implantable lead in said first linear configuration; said lead comprising:

(a) an electrically conductive electrode for being disposed in an electrical contact with a body organ;

(b) a flexible electrical conductor having a predetermined length and electrically coupled to said electrode;

(c) first means coupled to said lead and actuatable in response to the application of heat and force for being shaped initially to impart to said lead a second, non-linear configuration to dispose said electrode in efficient contact with a desired portion of the body organ, said first means comprising a flexible, insulating material;

(d) second means for providing an electrically insulating protective surface inert to body fluids and tissues and disposed about said lead;

(e) said insulating material having the property of being shaped at a temperature less than that temperature at which said second means is adversely affected; and (f) third means for receiving said rigid means, whereby said lead is reformed from said second non-linear configuration to said first linear configuration to facilitate the insertion of said lead into the body.

13. The combination as claimed in claim 12, wherein said third means defines an opening extending along substantially the entire length of said lead for receiving said elongated means.

14. The method of assembling and accurately locating a body implantable lead within a body to make electrical contact with a body organ, said lead comprising an electrically conductive electrode for making electrical contact with the body organ, a flexible electrical conductor having a pre-determined length and electrically coupled to said electrode, first means coupled to said lead for imparting a first, non-linear configuration to said lead, and second means for providing an electrically insulating, protective surface inert to body fluids and tissues and disposed about said lead; said method comprising the steps of:

(a) incorporating said first means into said body implantable lead and providing said body implantable lead with a second, substantially linear configuration;

(b) heating said lead to a temperature less than that temperature at which said second means is degraded and shaping said first means from its second linear configuration to its first non-linear configuration;

(c) reforming and maintaining said lead into its second substantially linear configuration;

(d) inserting said lead into the body to make electrical contact with the body organ; and (e) discontinuing the straightening of said body lead to its second substantially linear configuration, whereby said lead resumes its first substantially non-linear configuration, and said lead is maintained in electrical contact with the body organ.

15. The method as claimed in claim 14, wherein said lead comprises an opening for receiving straightening means, and said step of shaping and maintaining is effected by inserting said straightening means into said opening, and said reshaping step is effected by withdrawing said straightening means from said opening.

16. The method as claimed in claim 14, wherein the step of heating raises the lead temperature to a temperature which is in excess of body temperature.

* * * * *